United States Patent [19]

Aoki et al.

[11] Patent Number: 4,624,698
[45] Date of Patent: * Nov. 25, 1986

[54] HERBICIDAL TETRAHYDROBENZOTHIAZOLYL-1,3,5-TRIAZINONE DERIVATIVES AND COMPOSITIONS THEREOF

[75] Inventors: Katsumichi Aoki; Takafumi Shida; Youichi Kanda; Keigo Satake; Shiro Yamazaki; Tsuneaki Chida, all of Iwaki, Japan

[73] Assignee: Kureha Kagaku Kogyo Kabushiki Kaisha, Tokyo, Japan

[*] Notice: The portion of the term of this patent subsequent to Dec. 31, 2002 has been disclaimed.

[21] Appl. No.: 695,178

[22] Filed: Jan. 25, 1985

[30] Foreign Application Priority Data

Feb. 3, 1984 [JP] Japan ................................. 59-19121

[51] Int. Cl.$^4$ ..................... A01N 43/78; A01N 43/64; C07D 417/04; C07D 413/04
[52] U.S. Cl. ............................................. 71/90; 71/92; 71/93; 544/113; 544/220
[58] Field of Search ............... 544/113, 220; 71/90, 71/92, 93

[56] References Cited

U.S. PATENT DOCUMENTS

| 3,696,101 | 10/1972 | Litt et al. | 544/220 |
| 3,780,051 | 12/1973 | Litt et al. | 544/220 |
| 4,020,065 | 4/1977 | Rathgeb | 544/220 |
| 4,561,877 | 12/1985 | Aoki et al | 71/90 |

FOREIGN PATENT DOCUMENTS

| 0122761 | 10/1984 | European Pat. Off. | 544/220 |
| 1447182 | 8/1973 | United Kingdom | 544/220 |

Primary Examiner—Henry R. Jiles
Assistant Examiner—J. G. Mullins
Attorney, Agent, or Firm—John P. White

[57] ABSTRACT

Disclosed herein is a derivative of tetrahydrobenzothiazolyl-1,3,5-triazinone represented by the formula (I):

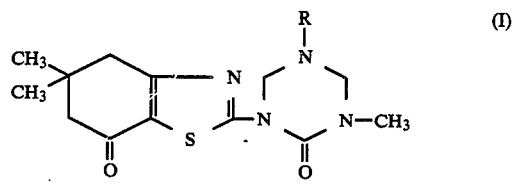

wherein R is a chemical group selected from the group consisting of 1-phenylethyl, 1-methylpropyl, 2-methylpropyl, allyl, 2-propynyl, cyclopropyl, cyclopentyl, phenyl, ethoxycarbonylmethyl, 2-tetrahydrofurylmethyl, 2-acetoxyethyl, 2-chloroethyl, 2-cyanoethyl, 2-hydroxyethyl, 2-methoxyethyl, 2,2-dimethoxyethyl, 2-(propionyloxy)ethyl, 2-(ethoxycarbonyl)ethyl, 2-(4-chlorobenzoyloxy)ethyl, 1-hydroxymethyl)propyl, 3-hydroxypropyl, 3-methoxypropyl, 3-acetoxypropyl, 3-morpholinopropyl and 3-(2-methylpiperidino)propyl, and a herbicidal composition containing the derivative as an active ingredient thereof.

8 Claims, 26 Drawing Figures

HERBICIDAL TETRAHYDROBENZOTHIAZOLYL-1,3,5-TRIAZINONE DERIVATIVES AND COMPOSITIONS THEREOF

SUMMARY OF THE INVENTION

In a first aspect of the present invention, there is provided a novel derivative of tetrahydrobenzothiazolyl-1,3,5-triazinone, represented by the formula(I):

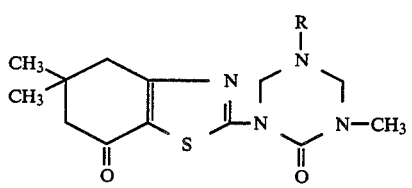

wherein R represents a chemical group selected from the group consisting of 1-phenylethyl, 1-methylpropyl, 2-methylpropyl, allyl, 2-propynyl, cyclopropyl, cyclopentyl, phenyl, ethoxycarbonylmethyl, 2-tetrahydrofurylmethyl, 2-acetoxyethyl, 2-chloroethyl, 2-cyanoethyl, 2-hydroxyethyl, 2-methoxyethyl, 2,2-dimethoxyethyl, 2-(propionyloxy)ethyl, 2-(ethoxycarbonyl)ethyl, 2-(4-chlorobenzoyloxy)ethyl, 1-(hydroxymethyl)propyl, 3-hydroxypropyl, 3-methoxypropyl, 3-acetoxypropyl, 3-morpholinopropyl and 3-(2-methylpiperidino)propyl.

In a second aspect of the present invention, there is provided a herbicidal composition comprising, as an active ingredient thereof, at least one of the compounds represented by the formula(I):

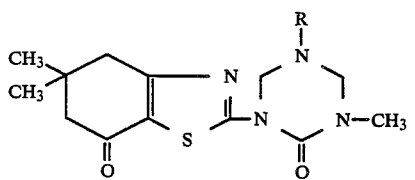

wherein R is a chemical group selected from the group consisting of 1-phenylethyl, 1-methylpropyl, 2-methylpropyl, allyl, 2-propynyl, cyclopropyl, cyclopentyl, phenyl, ethoxycarbonylmethyl, 2-tetrahydrofurylmethyl, 2-acetoxyethyl, 2-chloroethyl, 2-cyanoethyl, 2-hydroxyethyl, 2-methoxyethyl, 2,2-dimethoxyethyl, 2-(propionyloxy)ethyl, 2-(ethoxycarbonyl)ethyl, 2-(4-chlorobenzyloxy)ethyl, 1-(hydroxymethyl)propyl, 3-hydroxypropyl, 3-methoxypropyl, 3-acetoxypropyl, 3-morpholinopropyl and 3-(2-methylpiperidino)propyl, and a herbicidal carrier.

BACKGROUND OF THE INVENTION

The present invention relates to the novel derivatives of tetrahydrobenzothiazolyl-1,3,5-triazinone, represented by the formula(I):

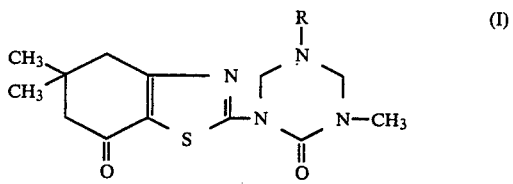

wherein R represents a chemical group selected from the group consisting of 1-phenylethyl, 1-methylpropyl, 2-methylpropyl, allyl, 2-propynyl, cyclopropyl, cyclopentyl, phenyl, ethoxycarbonylmethyl, 2-tetrahydrofurylmethyl, 2-acetoxyethyl, 2-chloroethyl, 2-cyanoethyl, 2-hydroxyethyl, 2-methoxyethyl, 2,2-dimethoxyethyl, 2-(propionyloxy)ethyl, 2-(ethoxycarbonyl)ethyl, 2-(4-chlorobenzoyloxy)ethyl, 1-(hydroxymethyl)propyl, 3-hydroxypropyl, 3-methoxypropyl, 3-acetoxypropyl, 3-morpholinopropyl and 3-(2-methylpiperidino)propyl.

As a result of the present inventors' studies concerning novel compounds showing favorable herbicidal activity, they have found that the novel derivatives of tetrahydrobenzothiazolyl-1,3,5-triazinone show excellent practical herbicidal activity and have attained the present invention.

BRIEF EXPLANATION OF DRAWINGS

Of the attached drawings.

DETAILED DESCRIPTION OF THE INVENTION

Figure 1:
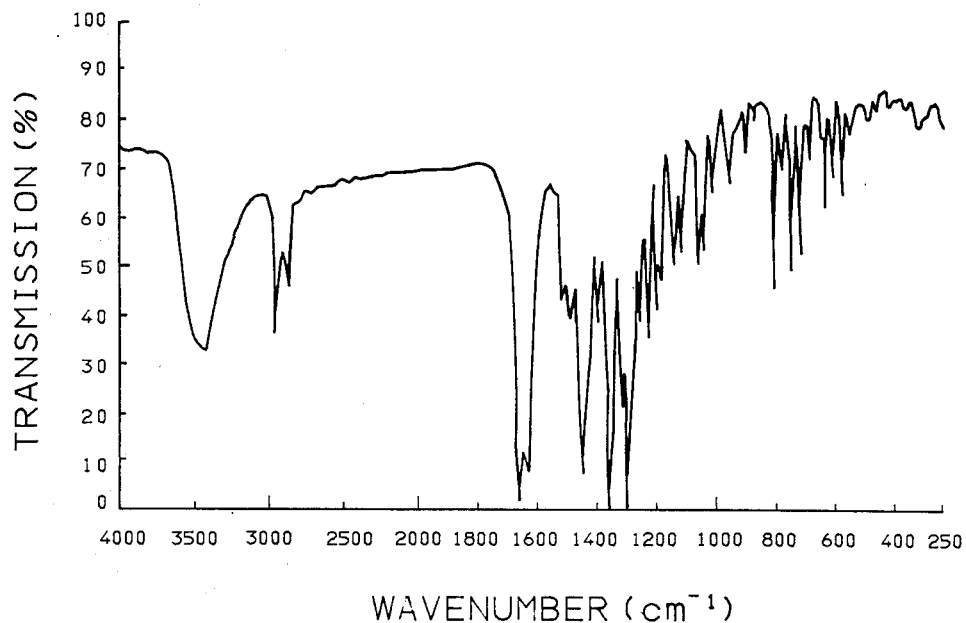
FIGS. 1 to 26 are the respective infrared absorption spectra of the derivatives of tetrahydrobenzothiazolyl-1,3,5-triazinone according to the present invention, the respective numbers of FIGS. 1 to 26 corresponding to the compound number of the derivatives of the present invention.
Figure 2:
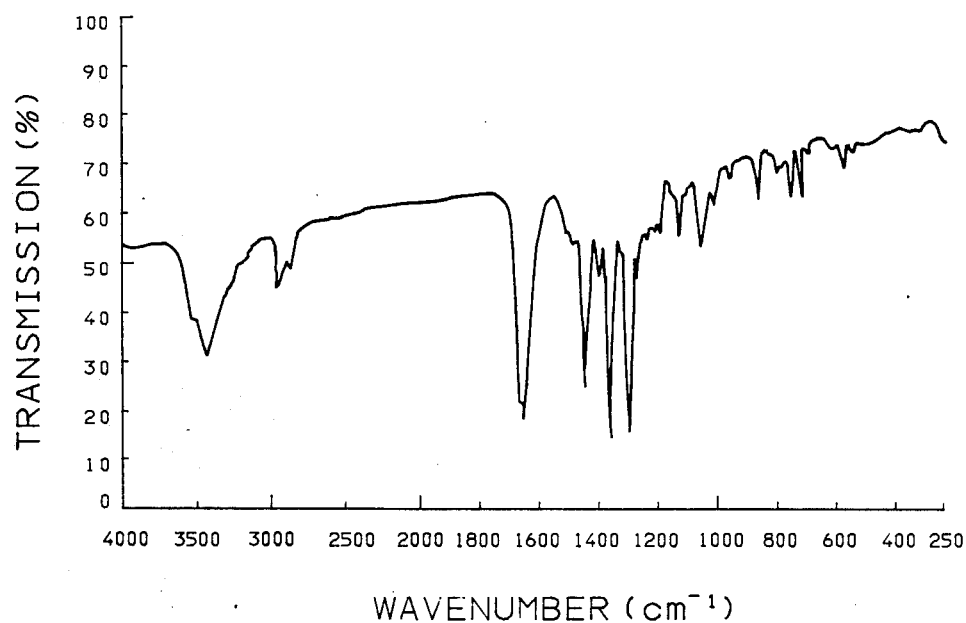
Figure 3:
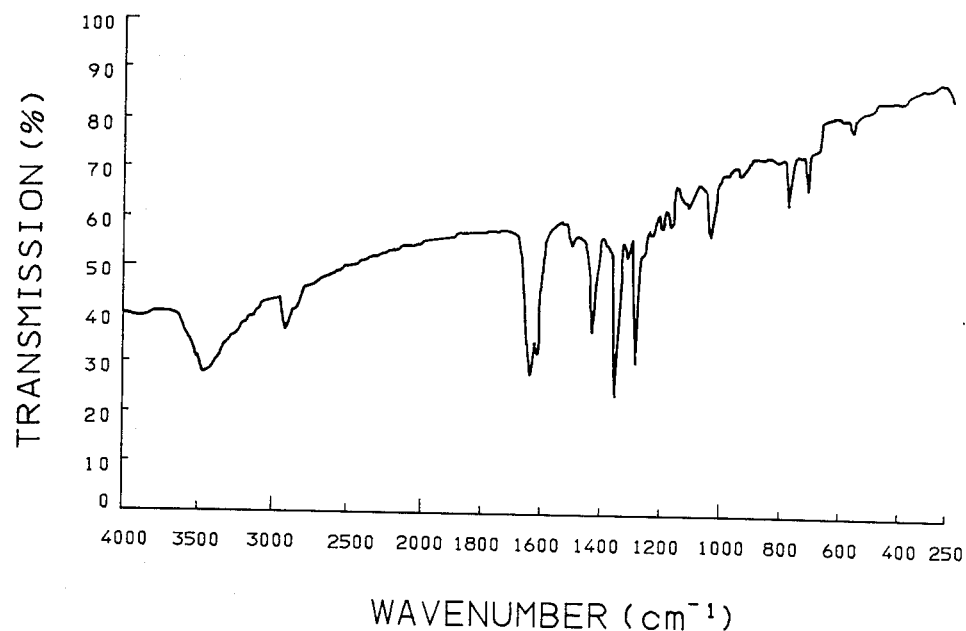
Figure 4:
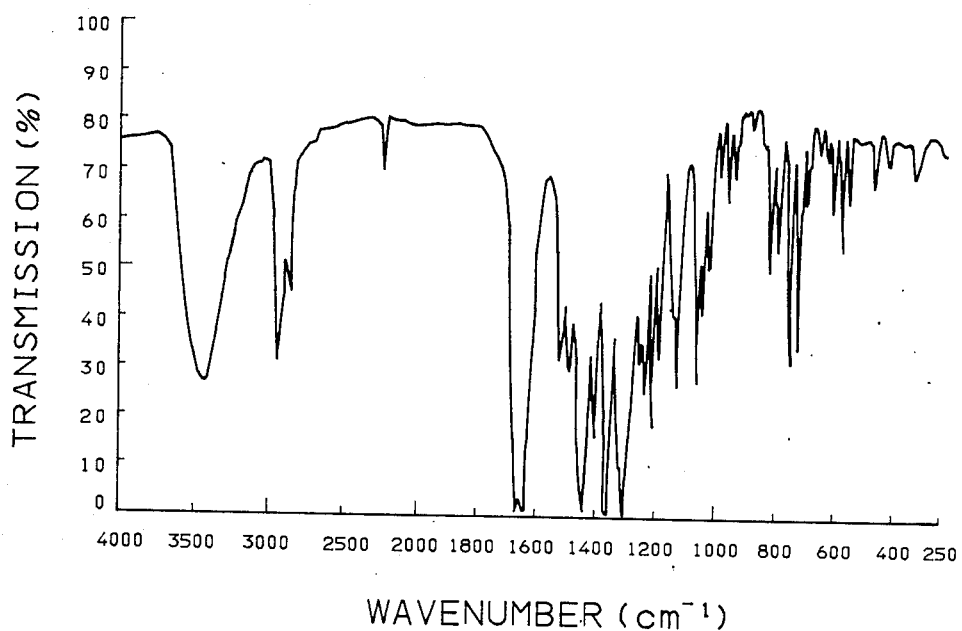
Figure 5:
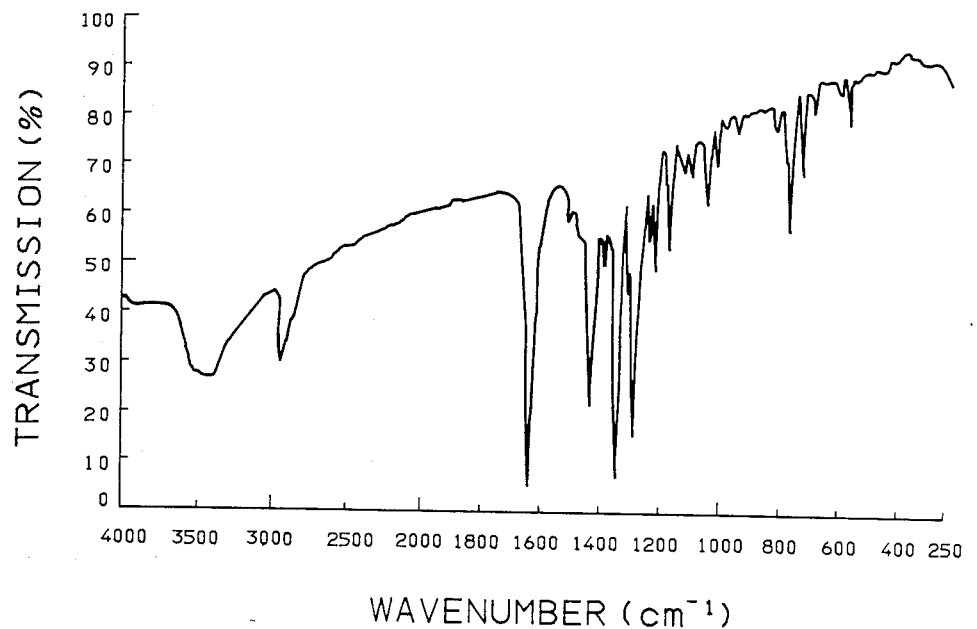
Figure 6:
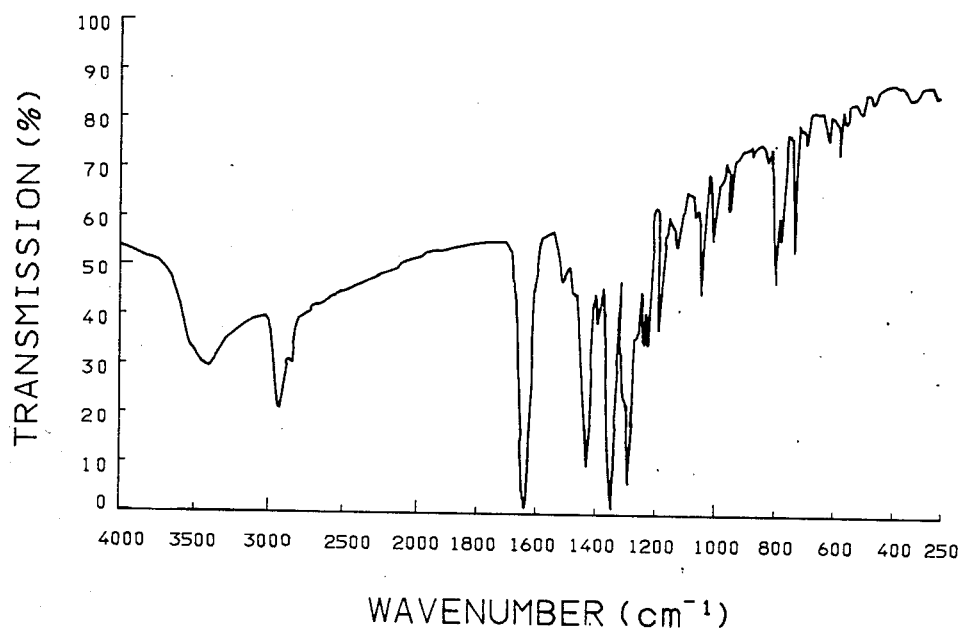
Figure 7:
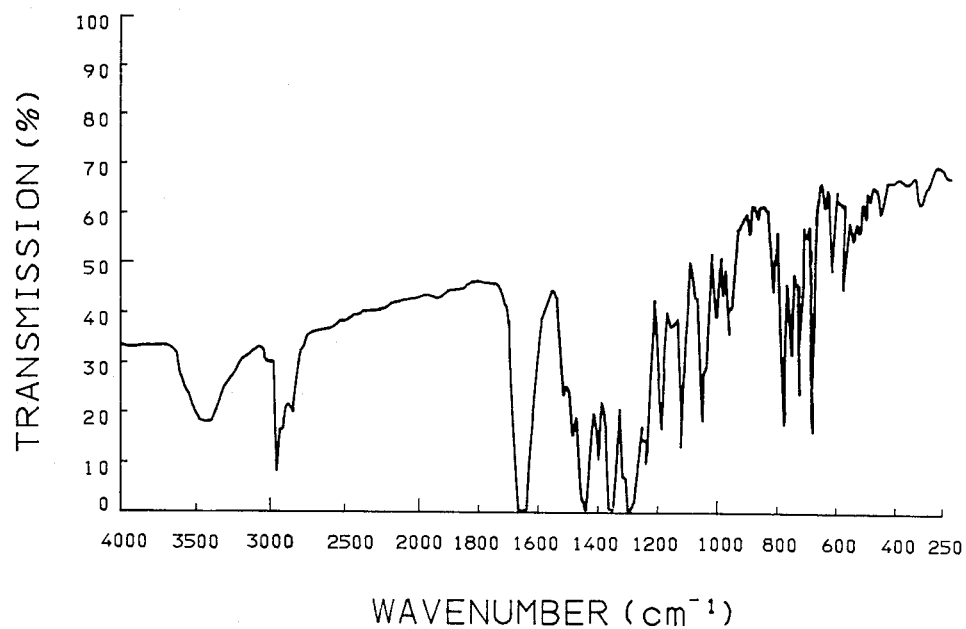
Figure 8:
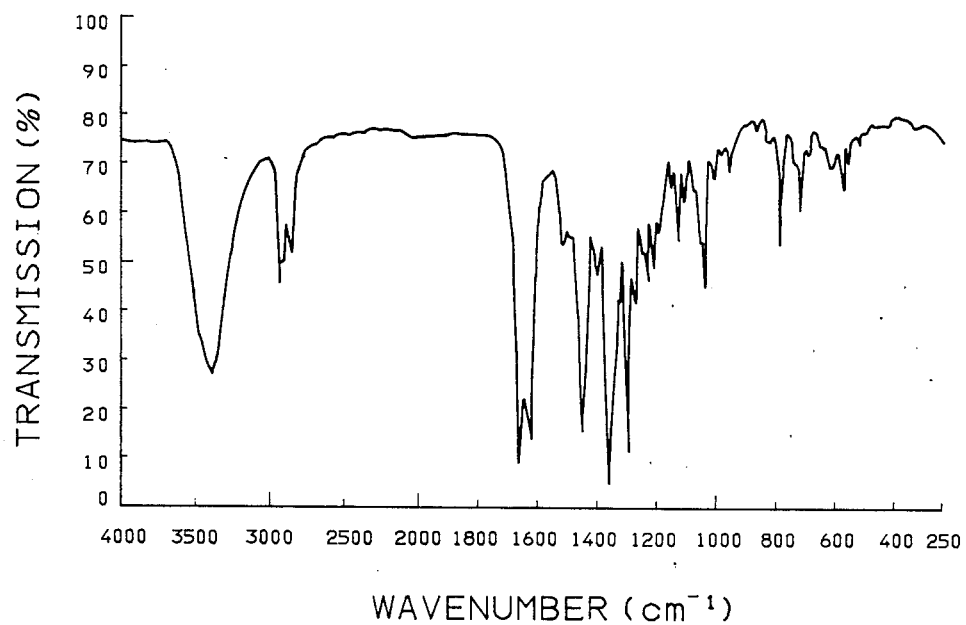
Figure 9:
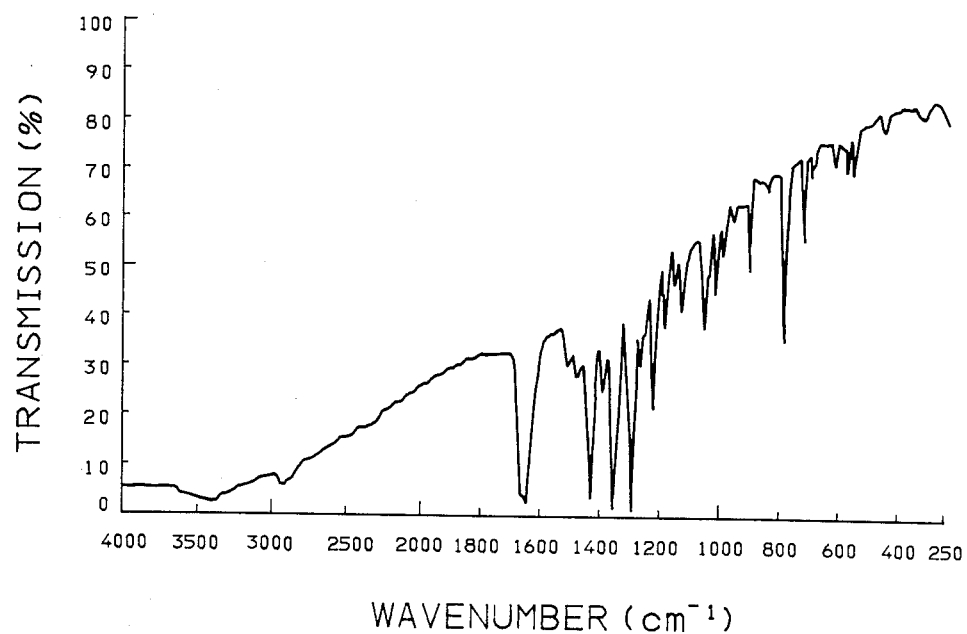
Figure 10:
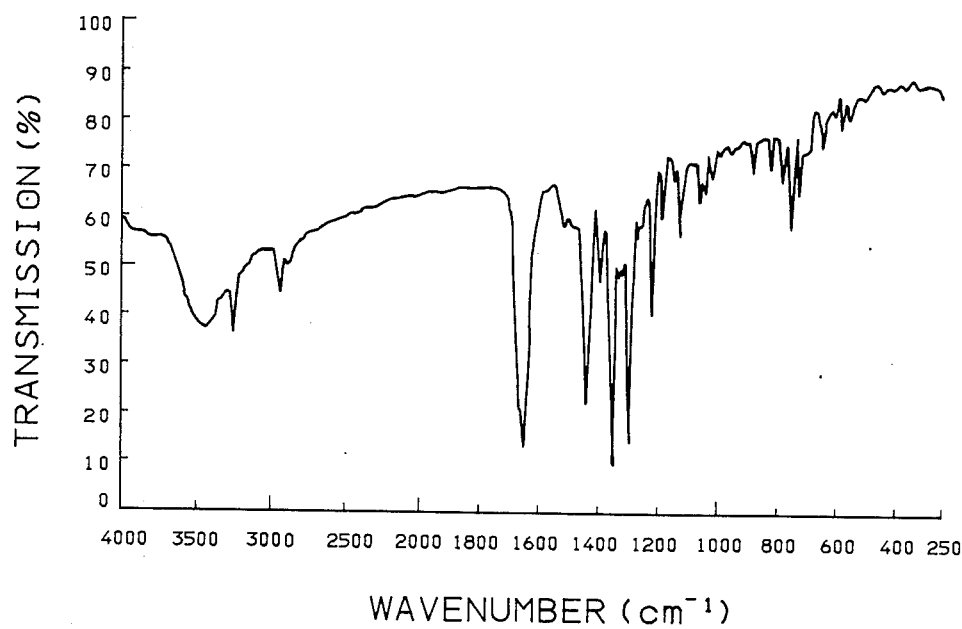
Figure 11:
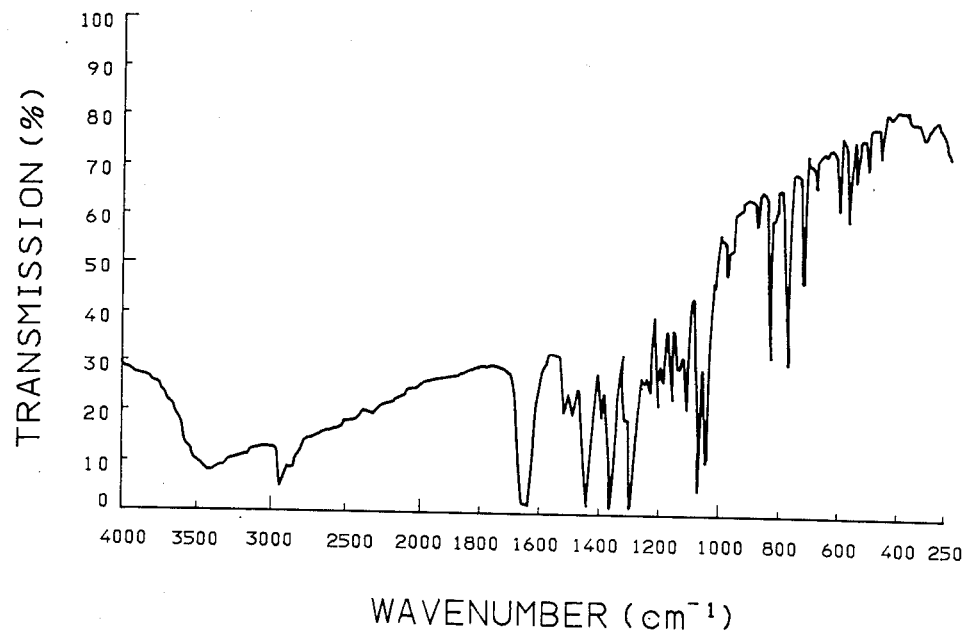
Figure 12:
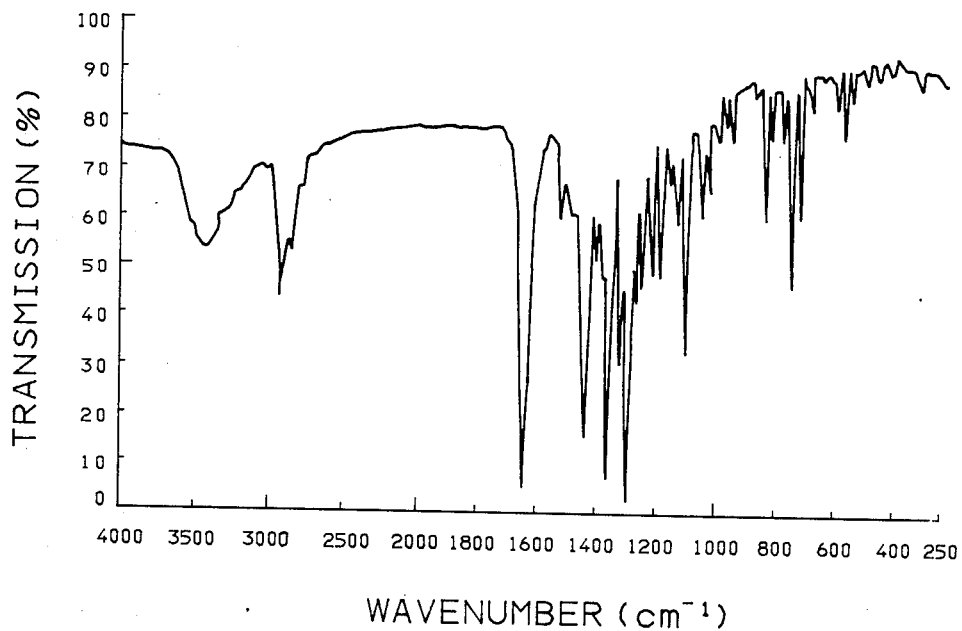
Figure 13:
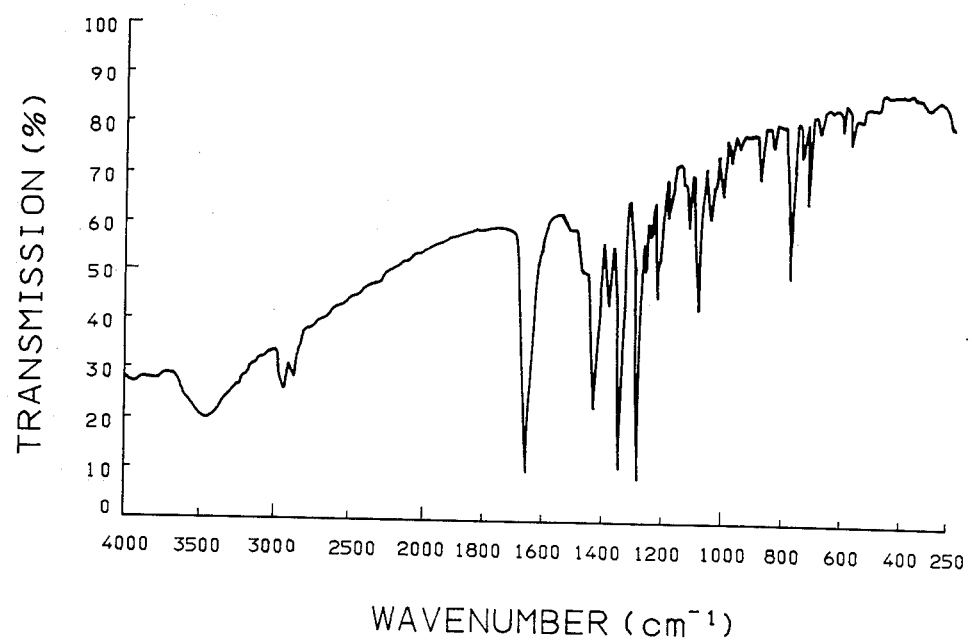
Figure 14:
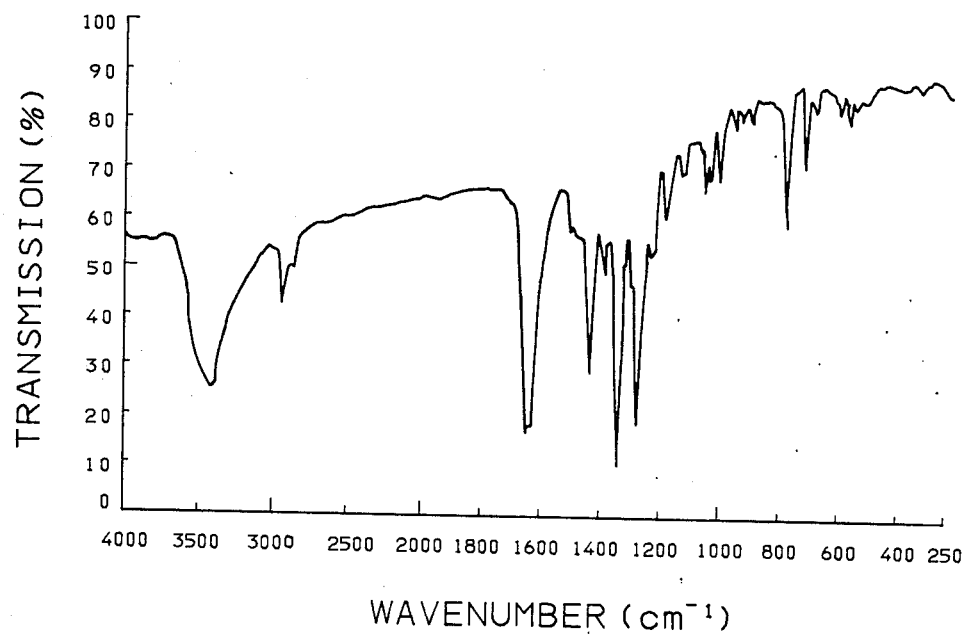
Figure 15:
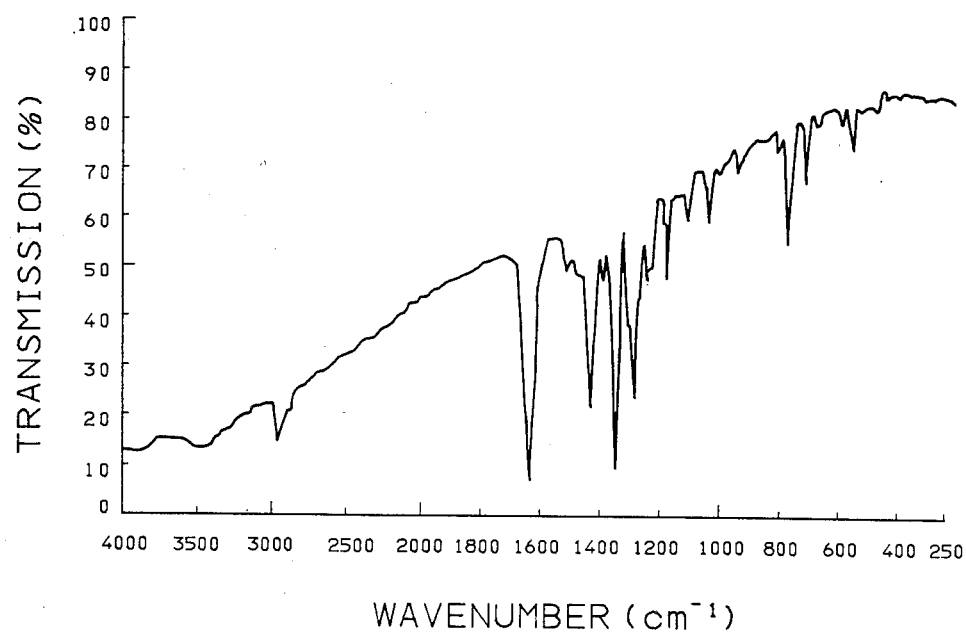
Figure 16:
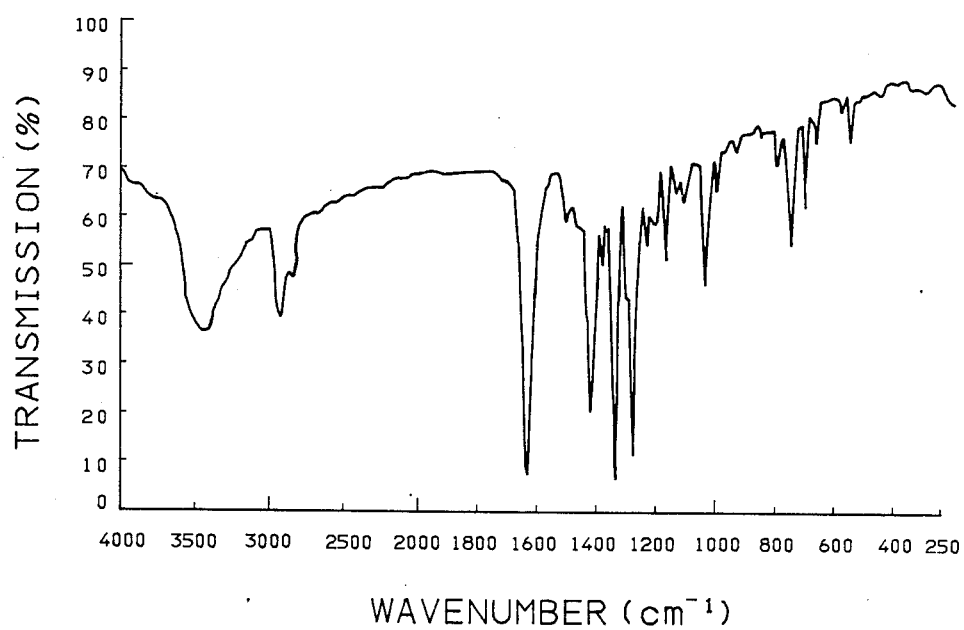
Figure 17:
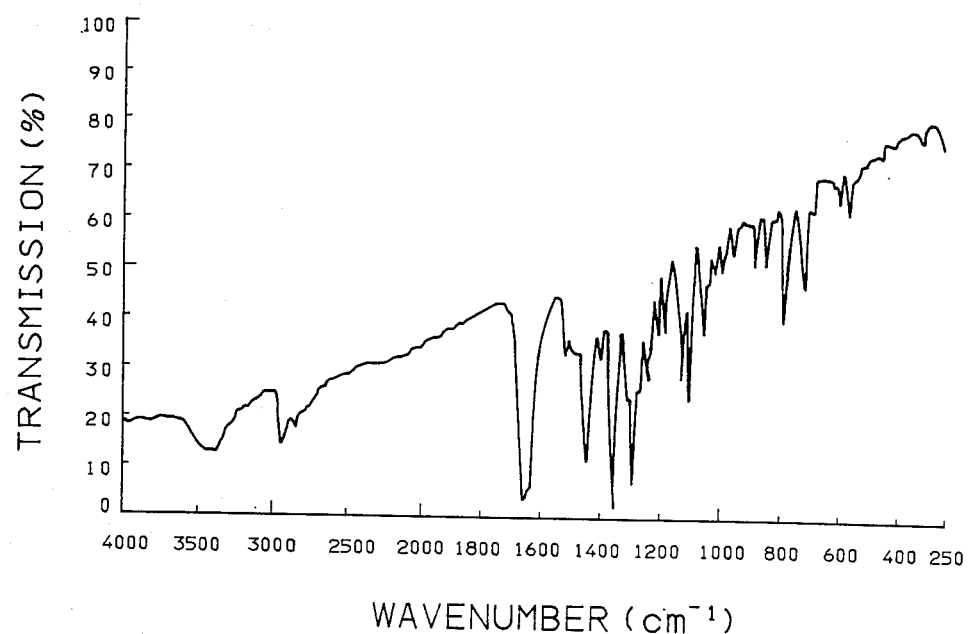
Figure 18:
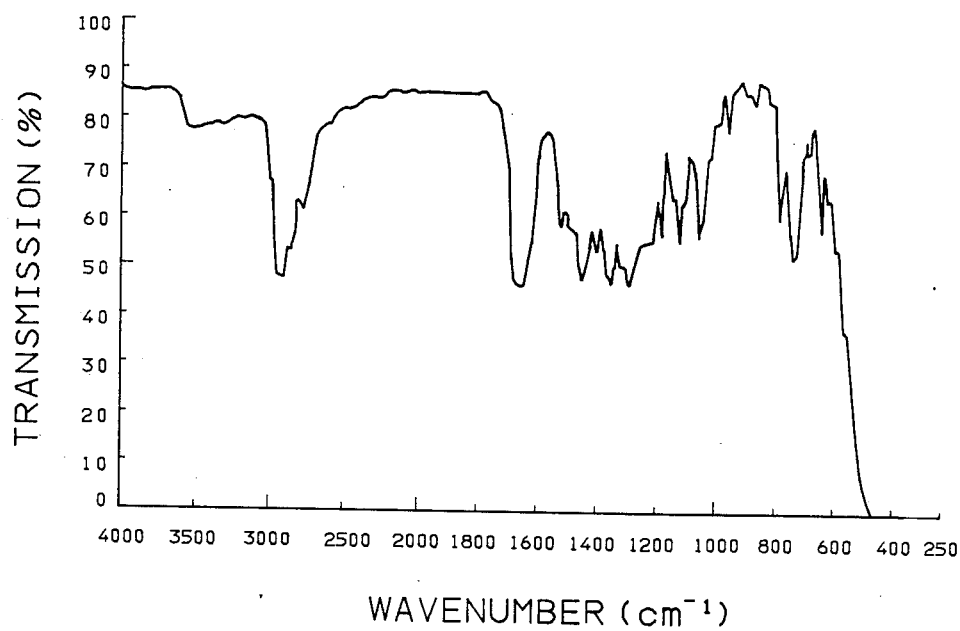
Figure 19:
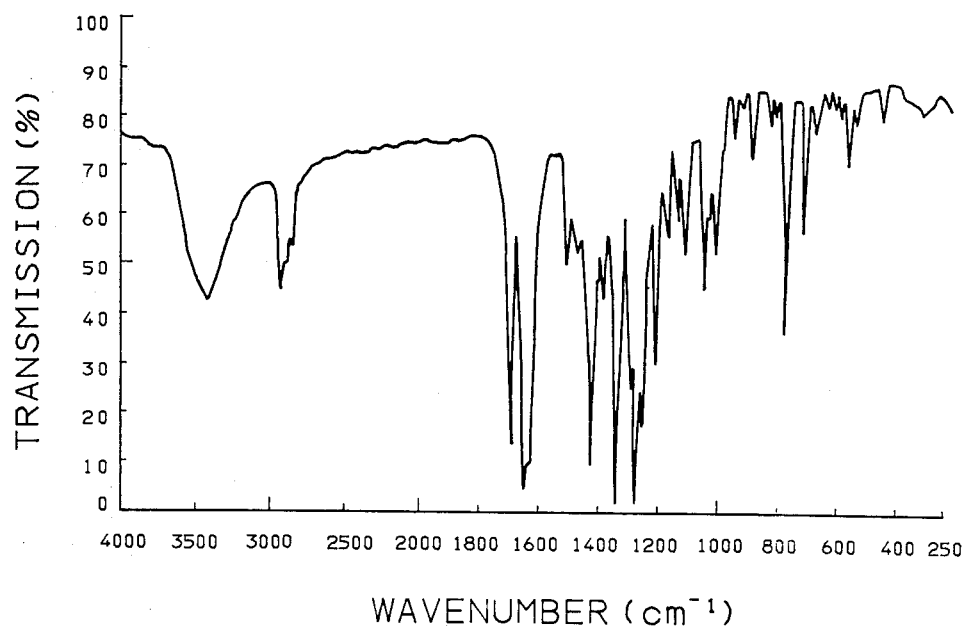
Figure 20:
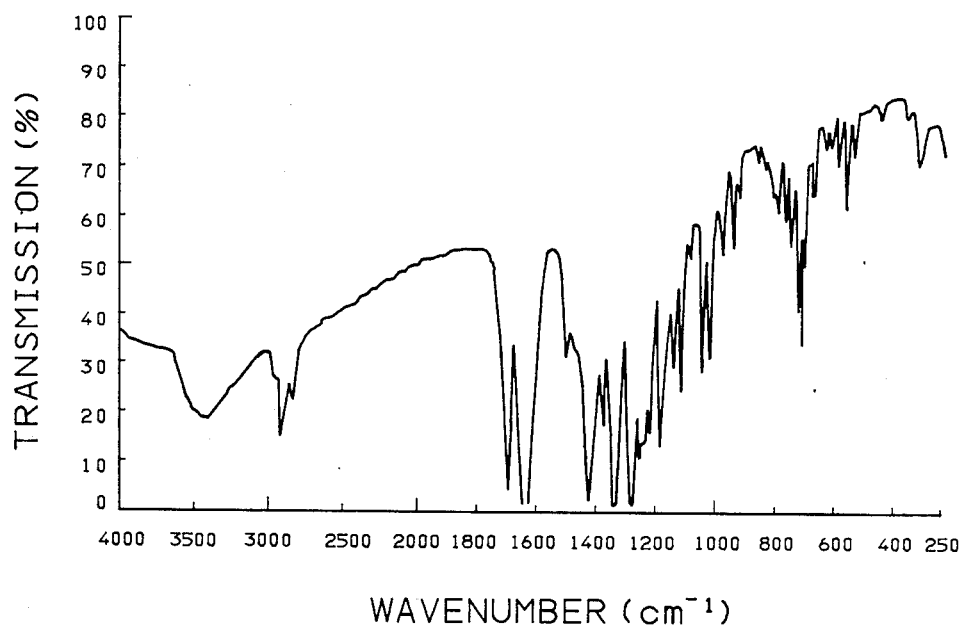
Figure 21:
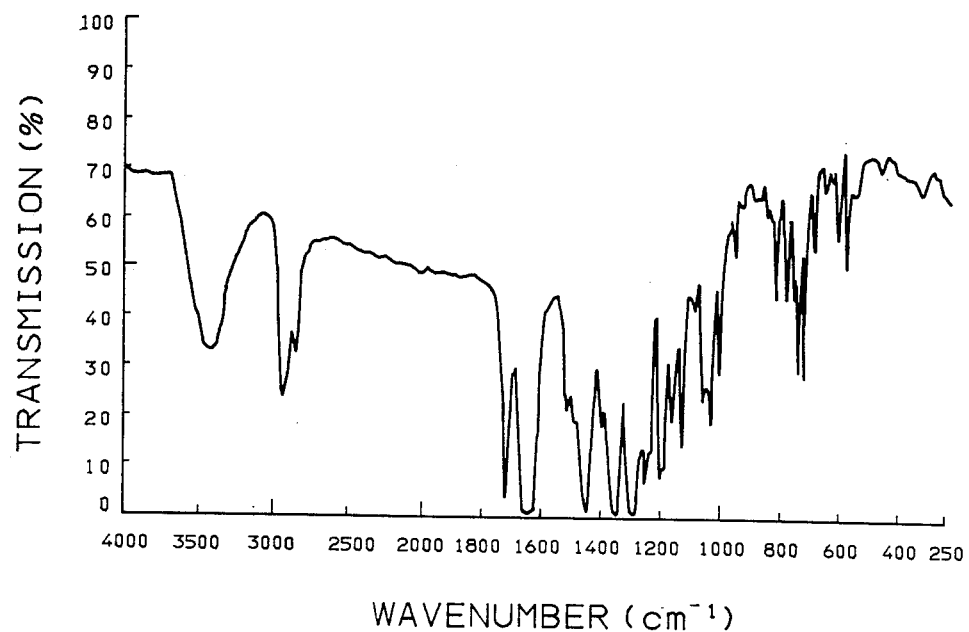
Figure 22:
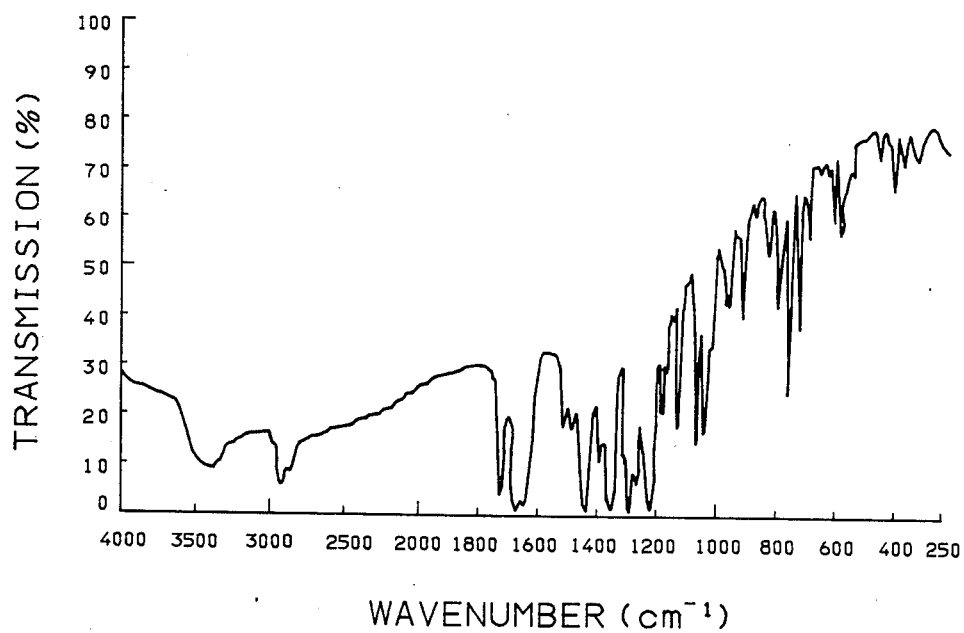
Figure 23:
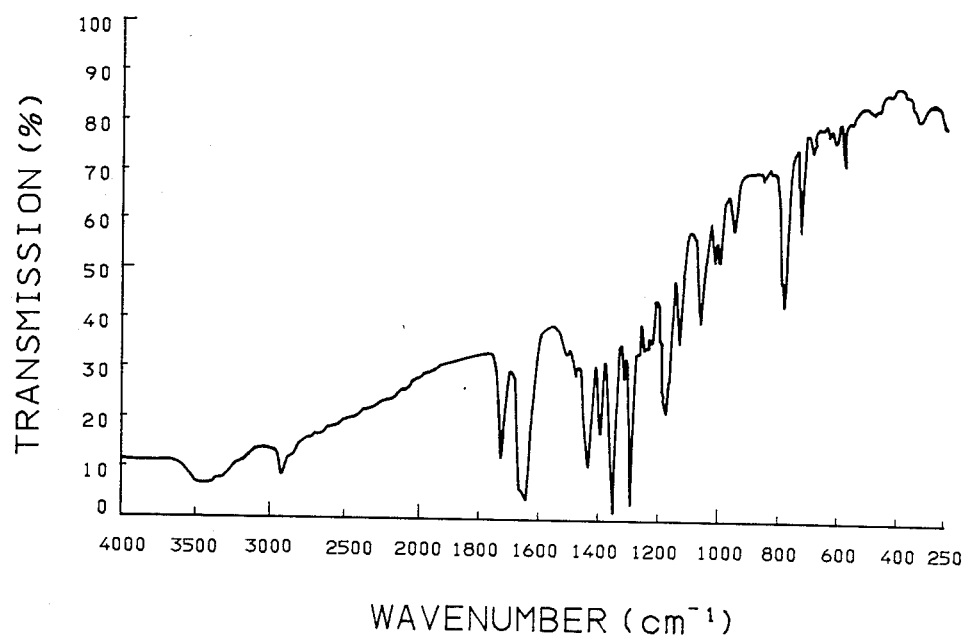
Figure 24:
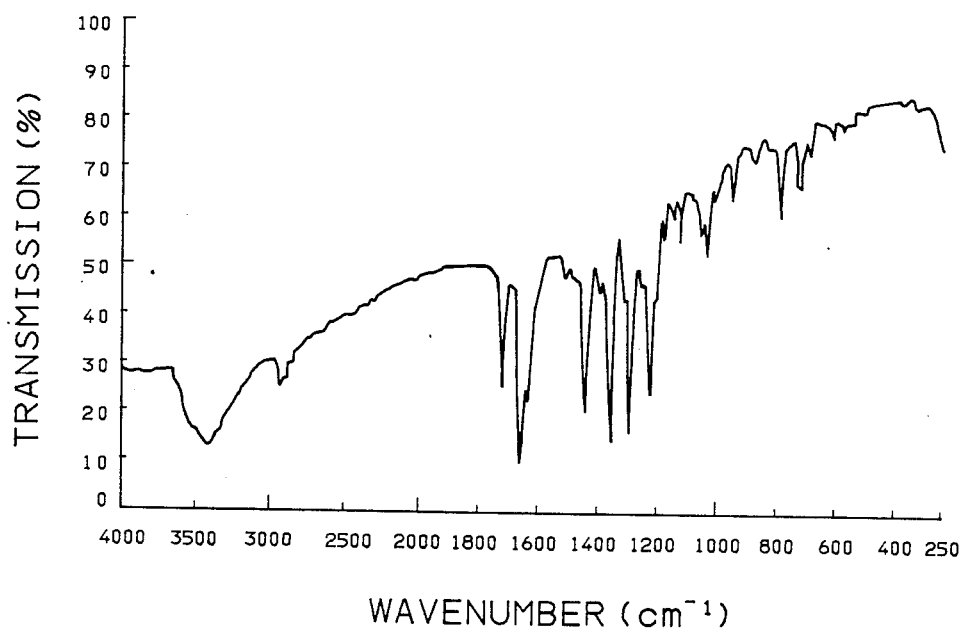
Figure 25:
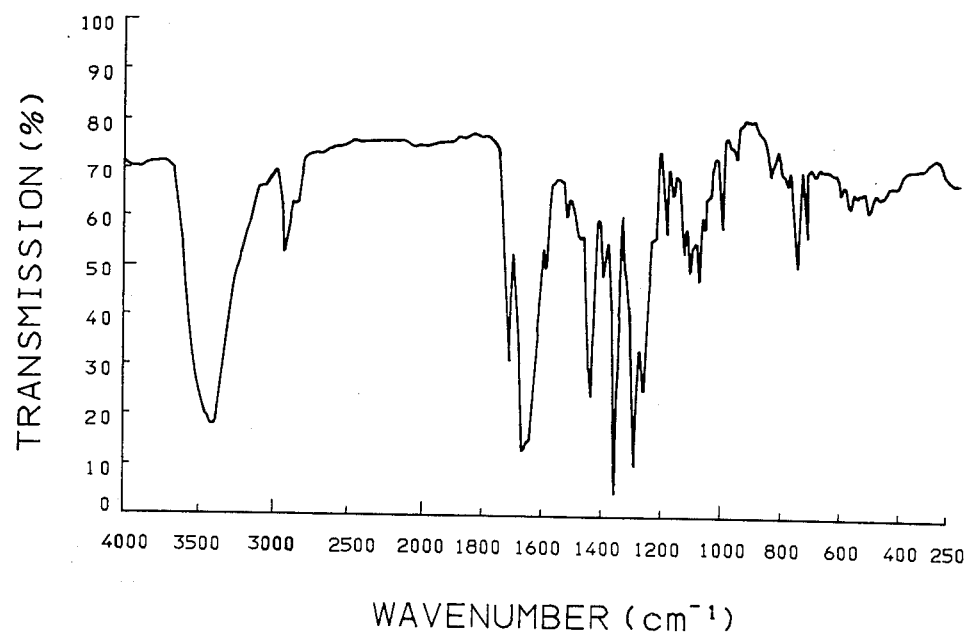
Figure 26:
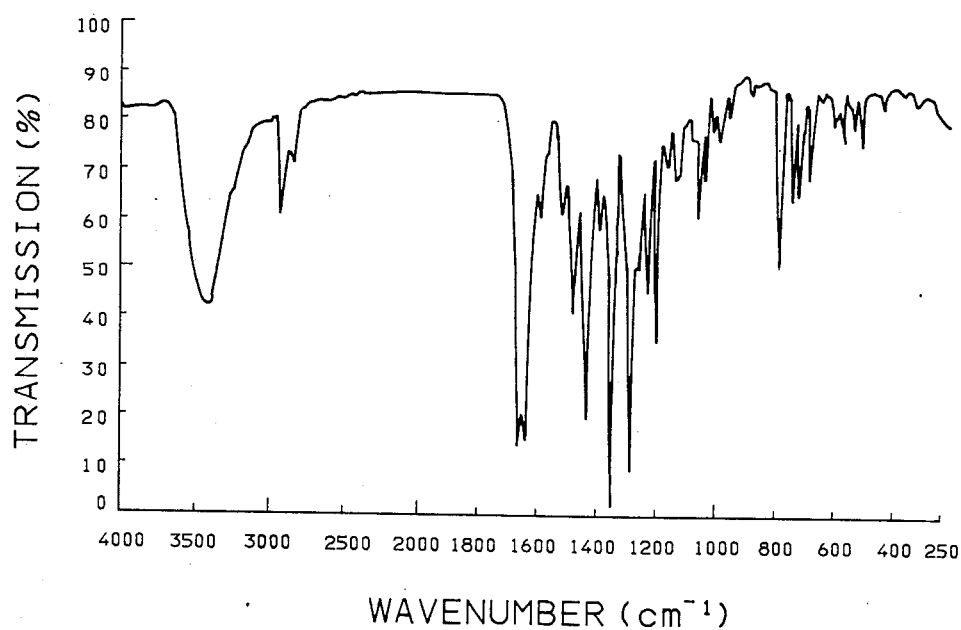

Each of the derivatives of tetrahydrobenzothiazolyl-1,3,5-triazinone according to the present invention (hereinafter referred to as the present compounds), represented by the formula(I) shows an excellent herbicidal activity on the gramineous weeds and the broad-leaved weeds in the foliage application tests, particularly on the broad-leaved weeds. As the range of application of the present compounds as herbicide, arable lands such as paddy field, general crop fields and orchards as well as non-arable lands may be mentioned.

The present compounds having a herbicidal activity, represented by the formula(I) can be synthesized by reacting formaldehyde and a primary amine with the compound, N-(4,5,6,7-tetrahydro-5,5-dimethyl-7-oxobenzothiazolyl)-N'-methylurea, represented by the formula(II) in a non-protonic solvent such as dimethylformamide (hereinafter referred to as DMF) according to the reaction formula shown below.

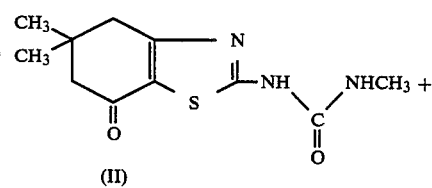

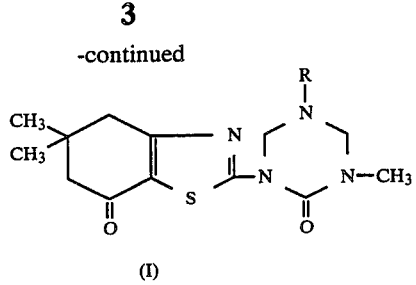

(I)

In addition, of the present compounds represented by the formula(I), the compound in which R is

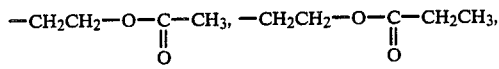

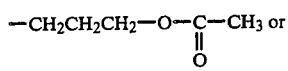

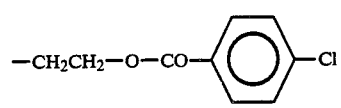

can be synthesized by reacting an acid chloride with a compound represented by the formula(I) wherein R represents —CH$_2$CH$_2$OH or —CH$_2$CH$_2$CH$_2$OH in chloroform as a solvent and in the presence of an acid acceptor such as a tertiary amine.

The compound represented by the formula(II) and used as the starting compound in the reaction shown by the above-mentioned reaction formula is obtained by reacting 2-amino-5,5-dimethyl-7-oxo-4,5,6,7-tetrahydrobenzothiazol with methyl isocyanate in a non-protonic solvent such as DMF.

In the case where a compound represented by the formula(I) is synthesized under the above-mentioned reaction formula, one equivalent of a compound represented by the formula(II) is reacted with more than two equivalents of formaldehyde in a non-protonic solvent (preferably, DMF), and then one or a little more than one equivalent of a primary amine is reacted with the reaction mixture. In the above-mentioned reaction, it is preferable to add an aqueous 35% solution of formaldehyde slowly into the solution of the compound represented by the formula(II) in DMF while maintaining at a temperature of lower than 30° C. under agitation for about 30 min.

As the primary amine used in the above-mentioned reaction, 2-chloroethylamine, s-butylamine, allylamine, 2-methoxyethylamine, cyclopentylamine and the like may be mentioned.

In addition, in the case where the compound represented by the formula(I) wherein R is —CH$_2$—CH$_2$—O—CO—CH$_3$, —CH$_2$—CH$_2$—O—CO—CH$_2$—CH$_3$, —CH$_2$—CH$_2$—CH$_2$—O—CO—CH$_3$ or

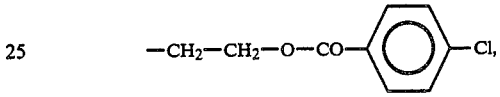

a compound represented by the formula(I) wherein R represents the group —CH$_2$CH$_2$OH or —CH$_2$CH$_2$CH$_2$OH is dissolved in dry chloroform, a tertiary amine such as triethylamine is added to the thus formed solution, thereby reacting the compound with the tertiary amine and then an acid chloride such as propionyl chloride is slowly added to the reaction mixture under cooling to carry out the reaction.

The physicochemical properties of each of the present compounds represented by the formula(I) are shown in Table 1.

TABLE 1

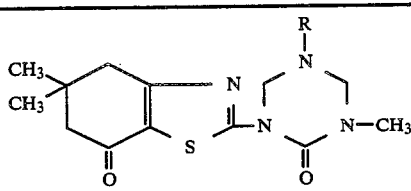

(I)

| No. of the present compound | Substituent R | Melting point (°C.) or (Refractive index, n$_D^{22}$) |
|---|---|---|
| 1 | 2-chloroethyl [—CH$_2$—CH$_2$—Cl] | 172–174 |
| 2 | 2-hydroxyethyl [—CH$_2$—CH$_2$—OH] | 149–151 |
| 3 | 3-hydroxypropyl [—CH$_2$—CH$_2$—CH$_2$—OH] | 149–150 |
| 4 | 2-cyanoethyl [—CH$_2$—CH$_2$—CN] | 185–186 |
| 5 | 2-methylpropyl [—CH$_2$—CH(CH$_3$)$_2$] | 169–171 |
| 6 | 1-methylpropyl [—CH(CH$_3$)—CH$_2$—CH$_3$] | 126–127 |
| 7 | 1-phenylethyl [—CH(CH$_3$)—C$_6$H$_5$] | 148–150 |
| 8 | 1-(hydroxymethyl)propyl [—CH(CH$_2$—OH)—CH$_2$—CH$_3$] | 120–121 |
| 9 | allyl [—CH$_2$—CH=CH$_2$] | 122–123 |
| 10 | 2-propynyl [—CH$_2$C≡CH] | 163–165 |
| 11 | 2,2-dimethoxyethyl [—CH$_2$—CH(OCH$_3$)$_2$] | 153–154 |
| 12 | 2-methoxyethyl [—CH$_2$—CH$_2$—OCH$_3$] | 136–137 |
| 13 | 3-methoxypropyl [—CH$_2$—CH$_2$—CH$_2$—OCH$_3$] | 127–128 |

TABLE 1-continued (I)

| No. of the present compound | Substituent R | | Melting point (°C.) or (Refractive index, $n_D^{22}$) |
|---|---|---|---|
| 14 | cyclopropyl | [−△] | 159–161 |
| 15 | cyclopentyl | [−⬠] | 181–183 |
| 16 | 2-tetrahydrofurylmethyl | [−CH$_2$−(tetrahydrofuryl)] | 138–139 |
| 17 | 3-morpholinopropyl | [−CH$_2$−CH$_2$−CH$_2$−N(morpholine)] | 150–151 |
| 18 | 3-(2-methylpiperidino)propyl | [−CH$_2$−CH$_2$−CH$_2$−N(2-methylpiperidine)] | (1.5515) |
| 19 | ethoxycarbonylmethyl [−CH$_2$−CO−O−CH$_2$−CH$_3$] | | 131–132.5 |
| 20 | 1-(methoxycarbonyl)ethyl [−CH(CH$_3$)−CO−O−CH$_3$] | | 110–112 |
| 21 | 1-(ethoxycarbonyl)ethyl [−CH(CH$_3$)−CO−O−CH$_2$−CH$_3$] | | 85–88 |
| 22 | 2-acetoxyethyl [−CH$_2$−CH$_2$−O−CO−CH$_3$] | | 104–106.5 |
| 23 | 2-(propionyloxy)ethyl [−CH$_2$−CH$_2$−O−CO−CH$_2$−CH$_3$] | | 117–118 |
| 24 | 3-acetoxypropyl [−CH$_2$−CH$_2$−CH$_2$−O−CO−CH$_3$] | | 113–115 |
| 25 | 2-(4'-chlorobenzoyloxy)ethyl | [−CH$_2$−CH$_2$−O−CO−C$_6$H$_4$−Cl] | 142–144 |
| 26 | phenyl | [−C$_6$H$_5$] | 165–167 |

The process for synthesizing the present compound is explained as follows and the infrared absorption spectra and the nuclear magnetic resonance spectra of the thus synthesized compounds of the present invention are shown as follows, wherein the positions of protons in the nuclear magnetic resonance spectra are given by the following numbering in the formula shown below.

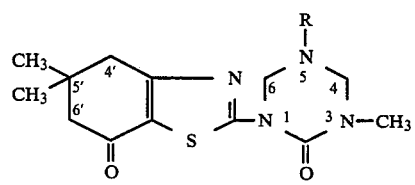

In the nuclear magnetic resonance spectrum (hereinafter referred to as NMR spectrum) of the following EXAMPLES, the abbreviations: s; d; t; q; sext and m mean respectively, the singlet-; doublet-; triplet-; quartet-; sextet- and multiple lines.

EXAMPLE 1

Synthesis of 5-(2-chloroethyl)tetrahydro-1-(4,5,6,7-tetrahydro-5,5-dimethyl-7-oxo-2-benzothiazolyl)-3-methyl-1,3,5-triazine-2(1H)-one (Compound No. 1)

Into 30 ml of DMF, 2 g (0.008 mol) of N-(4,5,6,7-tetrahydro-5,5-dimethyl-7-oxo-2-benzothiazolyl)-N-methylurea [a compound represented by the formula(II)] were dissolved, and 2.2 ml of an aqueous 35% solution of formaldehyde were slowly added to the thus formed solution at a temperature of lower than 30° C., and the mixture was stirred for about 30 min at that temperature.

Thereafter, 1.3 g (0.012 mol) of 2-chloroethylamine hydrochloride were added to the reaction mixture, and the thus obtained mixture was stirred for 3 hours at a temperature of lower than 30° C.

After collecting the thus educed crystals by filtration and washing the thus collected crystals with water, the thus washed crystals were recrystallized from ethanol to obtain 2 g of purified crystals pale yellow in colour melting at 172° to 174° C. in a yield of 71%. It was confirmed by examining the infrared absorption spectrum and nuclear magnetic resonance spectrum (hereinafter referred to as NMR spectrum) thereof, that the crystals were Compound No. 1.

NMR spectrum of Compound No. 1 (in CDCl$_3$), unit: ppm 1.12 (6H, s: CH$_3$ at 5' position), 2.4 (2H, s: CH$_2$ at 6' position), 2.73 (2H, s: CH$_2$ at 4' position), 3.0 (3H, s: N—CH$_3$ at 3 position), 3.13 (2H, t: J=6 Hz: N—CH$_2$ at 5 position), 3.65 (2H, t: J=6 Hz: N—CH$_2$—CH$_2$— at 5 position), 4.37 (2H, s: CH$_2$ at 4 position) and 5.15 (2H, s: CH$_2$ at 6 position).

EXAMPLE 2

Synthesis of 5-s-butyltetrahydro-1-(4,5,6,7-tetrahydro-5,5-dimethyl-7-oxo-2-benzothiazolyl)-3-methyl-1,3,5-triazine-2(1H)-one (Compound No. 6)

Into 20 ml of DMF, 1.5 g (0.006 mol) of the compound represented by the formula(II) were dissolved, and 1.65 ml of an aqueous 35% solution of formaldehyde were slowly added to the thus formed solution at a temperature of lower than 30° C. while maintaining the temperature of the mixture lower than 30° C. Thereafter, 0.4 g (0.006 mol) of s-butylamine was added to the mixture under cooling, and the thus obtained mixture was stirred for about 4 hours at a temperature of lower than 30° C. After collecting the thus educed crystals by filtration and washing the thus collected crystals with water, the crystals were recrystallized from ethanol to obtain 1.4 g of white crystals melting at 126°–127° C. in a yield of 68%. From the infrared absorption spectrum (hereinafter referred to as IR spectrum) and the following NMR spectrum of the thus obtained crystals, it was confirmed that the crystals were Compound No. 6:

NMR spectrum of Compound No. 6 (in CDCl$_3$) units: ppm. 1.02 (3H, t, J=6 Hz:

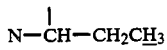

at 5 position), 1.1 (3H, d, J=6 Hz:

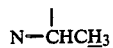

at 5 position), 1.1 (6H, s: CH$_3$ at 5' position), 1.25–1.85 (2H, m:

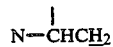

at 5 position), 2.4 (2H, s: CH$_2$ at 6' position), 2.75 (2H, s: CH$_2$ at 4' position), 2.95 (1H, sextet J=6 Hz:

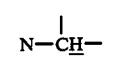

at 5 position), 3.0 (3H, s: N—CH$_3$ at 3 position), 4.37 (2H, s: CH$_2$ at 4 position) and 5.15 (2H, s: CH$_2$ at 6 position).

EXAMPLE 3

Synthesis of 5-allyltetrahydro-1-(4,5,6,7-tetrahydro-5,5-dimethyl-7-oxo-2-benzothiazolyl)-3-methyl-1,3,5-triazine-2(1H)-one (Compound No. 9)

Into a solution of 1.5 g (0.006 mol) of the compound represented by the formula(II) in 20 ml of DMF, 1.65 ml of an aqueous 35% solution of formaldehyde were slowly added while maintaining the temperature of the mixture lower than 30° C. After continuing stirring of the mixture for about 30 min, 0.34 g (0.006 mol) of allylamine was added to the mixture, and the thus obtained mixture was stirred for about 3 hours at a temperature of lower than 30° C., and then the mixture was heated to 65° to 70° C. and was stirred for 2 hours at the temperature.

After distilling DMF off from the reaction mixture, the residue was filtered to collect the solid matter which was washed with water. The thus washed solid matter was recrystallized from ethanol to obtain 1.5 g of white crystals melting at 122° to 123° C. in a yield of 75%.

It was confirmed from the IR spectrum and the following NMR spectrum of the crystals that the thus obtained crystals were Compound No. 9.

NMR spectrum of Compound No. 9 (in CDCl$_3$), unit: ppm. 1.1 (6H, s: CH$_3$ at 5' position), 2.4 (2H, s: CH$_2$ at 6' position), 2.73 (2H, s: CH$_2$ at 4' position), 3.0 (3H, s: N—CH$_3$ at 3 position), 3.41 (2H, d, J=6 Hz: N—CH$_2$ at 5 position), 4.31 (2H, s: CH$_2$ at 4 position), 5.15 (2H, s: CH$_2$ at 6 position), 4.9 to 5.4 (2H, m: CH=CH$_2$ at 5 position) and 5.67 to 6.22 (1H, m: CH=CH$_2$ at 5 position).

EXAMPLE 4

Synthesis of tetrahydro-1-(4,5,6,7-tetrahydro-5,5-dimethyl-7-oxo-2-benzothiazolyl)-5-(2-methoxyethyl)-3-methyl-1,3,5-triazine-2(1H)-one (Compound No. 12)

Into a solution of 2 g (0.008 mol) of the compound represented by the formula(II) in 30 ml of DMF, 2.2 ml of an aqueous 35% solution of formaldehyde were slowly added at a temperature of lower than 30° C., and the mixture was stirred for ca. 30 min at the temperature. Thereafter, 0.6 g (0.008 mol) of 2-methoxyethylamine was added to the mixture, and the thus obtained mixture was stirred for 3 hours at a temperature of lower than 30° C. Subsequently, the mixture was heated to 65°-70° C. and was stirred for 2 hours at that temperature. After distilling DMF off from the reaction mixture and collecting the residual solid matter by filtration, the solid matter was washed with water and recrystallized from ethanol to obtain 2.4 g of white crystals melting at 136°-137° C. in a yield of 86%.

It was confirmed from the IR spectrum and the following NMR spectrum thereof that the crystals were Compound No. 12.

NMR spectrum (in CDCl$_3$), unit: ppm. 1.01 (6H, s: CH$_3$ at 5' position), 2.39 (2H, s: CH$_2$ at 6' position), 2.72 (2H, s: CH$_2$ at 4' position), 2.97 (2H, t, J=5 Hz: N—CH$_2$ at 5 position), 3.0 (3H, s: N—CH$_3$ at 3 position), 3.37 (3H, s: O—CH$_3$ at 5 position), 3.58 (2H, t, J=5 Hz: N—CH$_2$—CH$_2$— at 5 position), 4.4 (2H, s: CH$_2$ at 4 position) and 5.17 (2H, s: CH$_2$ at 6 position).

EXAMPLE 5

Synthesis of 5-cyclopentyltetrahydro-1-(4,5,6,7-tetrahydro-5,5-dimethyl-7-oxo-2-benzothiazolyl)-3-methyl-1,3,5-triazine-2(1H)-one (Compound No. 15)

Into a solution of 1.5 g (0.006 mol) of the compound represented by the formula(II) in 20 ml of DMF, 1.65 ml of an aqueous 35% solution of formaldehyde were slowly added at a temperature of lower than 30° C., and after stirring the mixture for about 30 min at the temperature, 0.5 g (0.006 mol) of cyclopentylamine was added to the mixture, and the thus obtained mixture was stirred for 3 hours at 25° to 30° C. and further for 2 hours while heating thereof to 65° to 70° C. After distilling DMF off from the reaction mixture, the residual solid matter was collected by filtration, washed with water and recrystallized from ethanol to obtain 1.6 g of white crystals melting at 181° to 183° C. in a yield of 76%.

It was confirmed from the IR spectrum and the following NMR spectrum of the white crystals that the crystals were Compound No. 15.

NMR spectrum (in CDCl$_3$) unit: ppm. 1.12 (6H, s: CH$_3$ at 5' position), 1.4 to 2.1 (8H, m: CH$_2$ of cyclopentyl ring at 5 position), 2.41 (2H, s: CH$_2$ at 6' position), 2.75 (2H, s: CH$_2$ at 4' position), 3.0 (3H, s: N—CH$_3$ at 3 position), 3.05 to 3.49 (1H, m: CH of cyclopentyl ring at 5 position), 4.39 (2H, s: CH$_2$ at 4 position) and 5.21 (2H, s: CH$_2$ at 6 position).

EXAMPLE 6

Synthesis of tetrahydro-1-(4,5,6,7-tetrahydro-5,5-dimethyl-7-oxo-2-benzothiazolyl)-3-methyl-5-(2-propionyloxyethyl)-1,3,5-triazine-2(1H)-one (Compound No. 23)

Into a solution of 1.5 g (0.0044 mol) of Compound No. 2 in 20 ml of dry chloroform, 0.5 g (0.006 mol) of triethylamine was added, and while cooling the mixture to 0° to 5° C., 0.45 g (0.005 mol) of propionyl chloride was added to the mixture dropwise.

After the addition was over, the thus obtained mixture was stirred for 6 hours while raising the temperature of the mixture to room temperature slowly, and the organic layer was collected, washed with water and dried on anhydrous sodium sulfate. The organic layer (a solution in chloroform) was concentrated, and the thus obtained viscous material was purified by silicagel-chromatography to obtain a solid material which was recrystallized from a mixture of chloroform and hexane to obtain 1 g of white crystals melting at 117° to 118° C. in a yield of 58%.

It was confirmed by the IR spectrum and the following NMR spectrum of the crystals that the crystals were Compound No. 23:

NMR spectrum (in CDCl$_3$) unit: ppm. 1.09 (6H, s: CH$_3$ at 5' position), 1.1 (3H, t, J=8 Hz: CH$_3$ at 5 position), 2.3 (2H, q, J=8 Hz: —O—CO—CH$_2$ at 5 position), 2.37 (2H, s: CH$_2$ at 6' position), 2.7 (2H, s: CH$_2$ at 4' position), 3.0 (2H, s: N—CH$_3$ at 3 position), 3.05 (2H, t, J=6 Hz: N—CH$_2$— at 5 position), 4.25 (2H, t, J=6 Hz: N—CH$_2$—CH$_2$—O— at 5 position), 4.4 (2H, s: CH$_2$ at 4 position) and 5.15 (2H, s: CH$_2$ at 6 position).

The herbicidal activity of the present compound represented by the formula(I) is explained as follows.

In the case where the compound is used as a herbicide, the compound itself directly, or after being diluted to a suitable concentration with a diluent, is applied onto the object by means of, for instance, scattering as in the case of a conventional herbicidal compound. As occasion demands, spreader(s), wetting agent(s) and sticking agent(s) may be added to the compound, and the thus formed composition may be used as a herbicidal composition.

In addition, even in the case where the present compound represented by the formula(I) is admixed with another physiologically active substance, there is no fear of the decomposition or the denaturation of the compound itself, or the decomposition or denaturation of the thus admixed physiologically active substance.

Accordingly, the present compound may be used together with another physiologically active substance(s) such as fungicide(s), insecticide(s), herbicide(s), plant growth regulator(s) and fertilizers, and may be used after being admixed therewith.

The kinds of carrier(s) or adjuvant(s) therefor, the mixing ratio of the compound to the carrier(s) or adjuvant(s) and the amount of active ingredient(s) in the herbicidal composition may be selected from the broad range.

EXAMPLE 7

Preparation of a wettable powder 50 parts of Compound No. 1, 5 parts of a salt of ligninsulfonic acid, 3 parts of a salt of alkylsulfonic acid and 42 parts of diatomaceous earth were mixed and the mixture was pulverized to prepare a wettable powder containing Compound No. 1 as the active ingredient. The wettable powder is used after diluting thereof with water to a suitable concentration.

EXAMPLE 8

Preparation of an emulsifiable concentrate

Twenty-five parts of Compound No. 3, 65 parts of xylene and 10 parts of polyoxyethylene alkylarylether were uniformly mixed together to prepare an emulsifiable concentrate as a herbicidal composition containing Compound No. 3 as the active ingredient. The thus obtained herbicidal composition is used after diluting thereof with water to a suitable concentration.

EXAMPLE 9

Preparation of a granular composition

After uniformly mixing 8 parts of Compound No. 5, 40 parts of bentonite, 45 parts of clay and 7 parts of ligninsulfonic acid, water was added to the thus prepared mixture, and the aqueous mixture was kneaded and processed into granular material by a extruder-type granulating machine. By drying the thus extruded granular material, a granular composition containing Compound No. 5 as the active ingredient was obtained. The product is directly scattered onto the object, for instance, a soil in field.

EXAMPLE 10

Herbicidal experiment by foliage application

Onto each colony of the following respective weed plants and crop plants grown in the respective pots to their 2 to 4 leaf stage, each of the diluted aqueous solutions respectively prepared from the present compounds shown in Table 1 following the procedures similar to those in Example 7 at the dosage of an active ingredient 300 grams per 10 ares was sprayed at a rate of 100 liters per 10 ares. The results (damage of the plants) are shown also in Table 2 with the indices of 6 grades of herbicidal effect shown below:

Species of week plants:

(1) *Echinochloa crus-galli*, (2) *Poa annua*, (3) *Cyperus iria*, (4) *Amaranthus lividus*, (5) *Chenopodium album*, (6) *Stellaria media*, (7) *Cardamine flexuosa* and (8) *Portulaca oleracea*.

Species of crop plants:

(9) soy bean, (10) maize and (11) wheat.

Indices of herbicidal effect:

| | |
|---|---|
| 5 | completely withered |
| 4 | |
| 3 | |
| 2 | intermediate between 5 and 0 |
| 1 | |
| 0 | the same as on not-applied plants |

TABLE 2

Herbicidal Effect
(Plant species shown by number)

| | Plant No. | | | | | | | | | | |
|---|---|---|---|---|---|---|---|---|---|---|---|
| | Weed plant | | | | | | | | crop plant | | |
| Compound No. | 1 | 2 | 3 | 4 | 5 | 6 | 7 | 8 | 9 | 10 | 11 |
| 1 | 2 | 2 | 3.5 | 5 | 5 | 5 | 5 | 5 | 1 | 0 | 2 |
| 2 | 2 | 2 | 3.5 | 5 | 5 | 5 | 5 | 5 | 2 | 0 | 2 |
| 3 | 5 | 5 | 5 | 5 | 5 | 5 | 5 | 5 | 2 | 0 | 1 |
| 4 | 2 | 2 | 4 | 5 | 5 | 5 | 5 | 5 | 0 | 0 | 0 |
| 5 | 1 | 1 | 0 | 5 | 5 | 5 | 5 | 5 | 0 | 0 | 0 |
| 6 | 5 | 4 | 2 | 5 | 5 | 5 | 5 | 5 | 2 | 0 | 0 |
| 7 | 1 | 0 | 1 | 3 | 2 | 3 | 4 | 3 | 0 | 0 | 0 |
| 8 | 2 | 2 | 3 | 5 | 5 | 5 | 5 | 5 | 1 | 0 | 0 |
| 9 | 5 | 4 | 2 | 5 | 5 | 5 | 5 | 5 | 2 | 0 | 0 |
| 10 | 4 | 3 | 2 | 5 | 5 | 5 | 5 | 3 | 1 | 0 | 0 |
| 11 | 3 | 4 | 3 | 5 | 5 | 5 | 5 | 5 | 2 | 0 | 1 |
| 12 | 4 | 5 | 3 | 5 | 5 | 5 | 5 | 5 | 2 | 0 | 2 |
| 13 | 5 | 5 | 4 | 5 | 5 | 5 | 5 | 5 | 2 | 0 | 1 |
| 14 | 3 | 3 | 3 | 5 | 5 | 5 | 5 | 5 | 2 | 0 | 2 |
| 15 | 1 | 3 | 2 | 5 | 5 | 5 | 5 | 5 | 0 | 0 | 0 |
| 16 | 5 | 4 | 3 | 5 | 5 | 5 | 5 | 5 | 2 | 0 | 2 |
| 17 | 2 | 2 | 2 | 5 | 5 | 5 | 5 | 5 | 2 | 0 | 0 |
| 18 | 5 | 3 | 2 | 5 | 5 | 5 | 5 | 5 | 0 | 0 | 0 |
| 19 | 5 | 2 | 2 | 5 | 5 | 5 | 5 | 5 | 2 | 0 | 0 |
| 20 | 4 | 4 | 3 | 5 | 5 | 5 | 5 | 5 | 2 | 0 | 1 |
| 21 | 5 | 3 | 3 | 5 | 5 | 5 | 5 | 5 | 2 | 0 | 1 |
| 22 | 3 | 2 | 1 | 5 | 5 | 5 | 5 | 5 | 2 | 0 | 0 |
| 23 | 4 | 2 | 2 | 5 | 5 | 5 | 5 | 5 | 2 | 0 | 1 |
| 24 | 4 | 3 | 3 | 5 | 5 | 5 | 5 | 5 | 1 | 0 | 1 |
| 25 | 3 | 1 | 1 | 4 | 4 | 3 | 4 | 2 | 0 | 0 | 0 |
| 26 | 1 | 1 | 1 | 4 | 2 | 3 | 3 | 1 | 0 | 0 | 0 |

What is claimed is:

1. A compound represented by the formula(I):

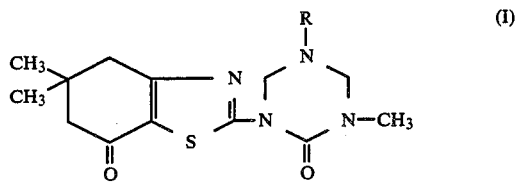

wherein R represents a chemical group selected from the group consisting of 1-phenylethyl, allyl, 2-propynyl, cyclopropyl, cyclopentyl, phenyl, ethoxycarbonylmethyl, 2-tetrahydrofurylmethyl, 2-acetoxyethyl, 2-chloroethyl, 2-cyanoethyl, 2-hydroxyethyl, 2-methoxyethyl, 2,2-dimethoxyethyl, 2-(propionyloxy)ethyl, 2-(ethoxycarbonyl)ethyl, 2-(4-chlorobenzoyloxy)ethyl, 1-(hydroxymethyl)propyl, 3-hydroxypropyl, 3-methoxypropyl, 3-acetoxypropyl, 3-morpholinopropyl and 3-(2-methylpiperidino)propyl.

2. A compound according to claim 1, wherein R is allyl group, cyclopropyl group, ethoxycarbonylmethyl group, 2-tetrahydrofurylmethyl group, 2-acetoxyethyl group, 2-methoxyethyl group, 2,2-dimethoxyethyl group, 2-(propionyloxy)ethyl group, 2-(ethoxycarbonyl)ethyl group, 3-hydroxypropyl group, 3-methoxypropyl group, 3-acetoxypropyl group or 3-(2-methylpiperidino)propyl group.

3. A compound according to claim 2, wherein R is 2-tetrahydrofurylmethyl group, 2-acetoxyethyl group, 2-methoxyethyl group, 2,2-dimethoxyethyl group, 2-(ethoxycarbonyl)ethyl group, 3-hydroxypropyl group, 3-methoxypropyl group or 3-(acetoxy)propyl group.

4. A compound according to claim 3, wherein R is 2-tetrahydrofurylmethyl group, 3-hydroxypropyl group or 3-methoxypropyl group.

5. A herbicidal composition comprising, as an active ingredient thereof, a herbicidally effective amount of at least one of the compounds represented by the formula(I):

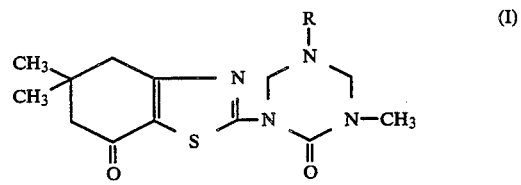

wherein R is a chemical group selected from the group consisting of 1-phenylethyl, allyl, 2-propynyl, cyclopropyl, cyclopentyl, phenyl, ethoxycarbonylmethyl, 2-tetrahydrofurylmethyl, 2-acetoxyethyl, 2-chloroethyl, 2-cyanoethyl, 2-hydroxyethyl, 2-methoxyethyl, 2,2-dimethoxyethyl, 2-(propionyloxy)ethyl, 2-(ethoxycarbonyl)ethyl, 2-(4-chlorobenzoyloxy)ethyl, 1-(hydroxymethyl)propyl, 3-hydroxypropyl, 3-methoxypropyl, 3-acetoxypropyl, 3-morpholinopropyl and 3-(2-methylpiperidino)propyl.

6. A herbicidal composition according to claim 5, wherein R is allyl group, cyclopropyl group, ethoxycarbonylmethyl group, 2-tetrahydrofurylmethyl group, 2-acetoxyethyl group, 2-methoxyethyl group, 2,2-dimethoxyethyl group, 2-(propionyloxy)ethyl group, 2-(ethoxycarbonyl)ethyl group, 3-hydroxypropyl group, 3-methoxypropyl group, 3-acetoxypropyl group or 3-(2-methylpiperidino)propyl group.

7. A herbicidal composition according to claim 6, wherein R is 2-tetrahydrofurylmethyl group, 2-acetoxyethyl group, 2-methoxyethyl group, 2,2-dimethoxyethyl group, 2-(ethoxycarbonyl)ethyl group, 3-hydroxypropyl group, 3-methoxypropyl group or 3-(acetoxy)propyl group.

8. A herbicidal composition according to claim 7, wherein R is 2-tetrahydrofurylmethyl group, 3-hydroxypropyl group or 3-methoxypropyl group.

* * * * *